United States Patent [19]

de Medinaceli

[11] Patent Number: 4,586,504
[45] Date of Patent: May 6, 1986

[54] NERVE CONNECTOR AND METHOD

[75] Inventor: Luis de Medinaceli, Annandale, Va.

[73] Assignee: Cell Medical Corporation, Hillsborough, N.C.

[21] Appl. No.: 745,788

[22] Filed: Jun. 17, 1985

[51] Int. Cl.⁴ .................. A61B 17/00; A61B 17/11
[52] U.S. Cl. ................................................ 128/335.5
[58] Field of Search ................ 128/334 R, 335.5, 335, 128/303.13, 334 C

[56] References Cited

U.S. PATENT DOCUMENTS 4,306,561 12/1981 de Medinaceli ................ 128/334 C

FOREIGN PATENT DOCUMENTS

82/04390 12/1982 PCT Int'l Appl. ............. 128/334 R

OTHER PUBLICATIONS

*Experimental Neurolog* 81 publication 488–496 (1983) title: "Peripheral Nerve Reconnection: . . . " authors: Lus de Medinaceli, William J. Freed, and Richard Jed Wyatt.

*Primary Examiner*—Richard C. Pinkham
*Assistant Examiner*—Gary Jackson
*Attorney, Agent, or Firm*—B. B. Olive

[57]  ABSTRACT

A method and device for rejoining the stumps of transected cable-like structures such as peripheral nerves are based on using a flexible, inelastic sheet of material as a connector. The connector has inscribed guide-measuring lines and guide points enabling the diameter of the nerve or other structure being reconnected to be measured as well as providing a way of measuring the stump lengths to be secured and trimmed to achieve optimum results.

10 Claims, 12 Drawing Figures

NERVE CONNECTOR AND METHOD

DESCRIPTION

1. Technical Field

This invention relates to surgery, and more specifically to a method and device for rejoining the proximal and distal stumps of transected cable-like structures such as peripheral nerves.

2. Background Art

A crush injury to a peripheral nerve does not destroy the endoneurial structures. The remaining basal lamina tubes provide the pathways that guide the regenerating neurites through the injured portion of nerve so that they reach their former peripheral connections. This is in sharp contrast with the consequences of a transection. At the zone of the cut, all pathways are destroyed and the guidance effect is lost. The sprouts or regenerating neurites, born in the proximal stump, will grow at random in the area of the cut. After suture, most sprouts will reach the distal stump and therefore penetrate structures that have not been damaged. From then on, they will follow steadily and blindly the guide they have found, without branching or changing direction. At the suture line, however, considerable interlacing of the regenerating fibers occurs, so that many neurites fail to enter the appropriate endoneurial tube in the distal stump.

The difference in functional recovery between crush injury and transection followed by suture is generally attributed to these anatomo-pathological characteristics. To decrease the interlacing of regenerating neurites in a transected and repaired nerve, it is necessaary to keep the fibers in good longitudinal alignment with their stumps, i.e., whorling of the nerve structures must be avoided. Keeping fibers in proper longitudinal alignment, however, is difficult. Nerve fibers are so soft that the slightest stress disrupts them and modifies their direction. In an undamaged nerve the continuity of the envelopes prevents any disorganization, but at the tip of a transected nerve, the neurites wave, whorl, and buckle. Suturing the stumps considerably worsens the situation. However fine the stiches are, they impose an irregular stress on the nerve. There is a combination of traction at the suture points and of slackness between them. The irregular stress on the sheaths results in a profound longitudinal disorganization of the fibers inside the fasciles.

A solution is suggested by the principal of de Saint-Venant, which deals with the repartition of tensile forces in elastic bodies (de Saint-Venant, A. 1856. *Memoire sur la torsion des prismes.* Mem. Acad. Sci. Paris, 14: 233–560). In the case of elastic cylinders submitted to axial tension, de Saint-Venant's principal states that only near the loaded end does the stress distribution depend on the manner of applying the tensile force; in cross sections at a sufficient distance from the end, the stresses are practically uniformly distributed. From this it can be postulated that if the situation were reversed, that is to say, if the traction were placed at an appropriate distance from the tip of the nerve stumps, there should be no stress inflicted on the nerve structures at the extremity of the stumps. Instead, there should be a very uniform displacement of the whole structure. This postulate provides a basis for a method of reunion. Under appropriate tension, a piece of material is stitched to the external sheath of nerve stumps at a sufficient distance from their tips. Thus, all mechanical stresses are isolated from the zone of repair and the stumps are smoothly pulled into contact.

The conclusions derived from this new postulate and their utility to nerve surgery were first applied in U.S. Pat. No. 4,306,561. Subsequently, the postulate was applied in the methodologies disclosed in: de Medinaceli, L., and W. J. Freed. 1983, *Peripheral Nerve Reconnection: Immediate Histological Consequences of Distributed Mechanical Support.* Exp. Neurol. 81: 459–468, and also: de Medinaceli, L., R. J. Wyatt, and W. J. Freed. 1983, *Peripheral Nerve Reconnection: Mechanical, Thermal and Ionic Conditions that Promote the Return of Function.* Exp. Neurol. 81: 469–488, and: de Medinaceli, L., W. J. Freed, and R. J. Wyatt. 1983, *Peripheral Nerve Reconnection: Improvement of Long Term Functional Effects under Simulated Clinical Conditions in the Rat.* Exp. Neurol. 81: 488–496. These articles teach the use of a square, elastic piece of rubber as a connecting member for joining the stumps of a transected nerve fiber without stitches at the point of transection. In such procedure, the tensile properties of the rubber connector are used to draw the stumps of the nerve fibers towards each other after they have been stitched to the connecting piece. This method is satisfactory for some species of laboratory animals since it is possible to select the nerve of the appropriate dimensions, i.e., to predetermine the mechanical resistance and elasticity of the organ and therefore of the device. Moreover, connections which are based on mere approximations are acceptable for exploratory research in experimental animals. For human surgery, however, the use of an elastic connector is unsatisfactory because it is not practical to modify the elasticity of the connector to match the unlimited variations of the mechanical properties of nerves. Furthermore, the described method requires a great deal of trial and error during each surgical session before the operator is able to determine exactly how much tissue must be trimmed from each nerve stump and to what extent the nerve can be stretched when the trimmed stumps are drawn towards one another. Trimming too little nerve tissue from the stumps is disadvantageous because those areas closest to the tips of the stumps typically suffer the greatest traumatic damage and are preferably removed. Trimming too much tissue from the stumps, however, will require the surgeon to place the nerve under an unacceptably high degree of tension when the stumps are joined. It is well known that this increases the likelihood of mechanical and vascular damage to the nerve, resulting in the formation of adverse scar tissue or even in the pulling apart of the joined stumps in the post-operative period. Moreover, it would be desirable to place that portion of the rejoined nerve lying between the two suture points, and having the transected zone in the middle, under slight compression. Nothing in the prior art teaches the surgeon how to balance this interest in increasing compression in one portion of the nerve against the desire to avoid increasing tension in the remainder of the nerve. Finally, all of these factors will vary, depending upon the diameter and the type of the nerve being repaired. Even a well-trained operator would often fail to determine the necessary parameters and would therefore make an unsatisfactory repair.

What is needed is a connecting device which tells the surgeon precisely how much tissue to trim away from the proximal and distal stumps of severed nerves, how much compression to use at the site of reunion, and how much traction to exert on the remote portions of the nerve. The device must hold the stumps together without any foreign material at the zone of reunion and must not disrupt the nerve structures and alignment in this area. The device must allow for the differences in elastic retraction between nerve envelopes and nerve tissue. The device must ensure the possibility of rotational alignment of the stumps and must permit fine adjustment of this alignment. The device must be adaptable to all of the different diameters of peripheral nerves that the surgeon is likely to encounter. The device must not exert any circular pressure on the nerve structures and must allow for expansion of these structures in case of post-operative edema. The applicant, however, is unaware of any prior art connecting device either providing such information or allowing the operator to implement such information, and applicant is unaware of any independent source of such information in the prior art. The provision of a method and device having the mentioned desired characteristics thus becomes the object of the invention.

DISCLOSURE OF THE INVENTION

In accordance with the present invention, applicant provides a nerve-connecting device on which are transcribed the lines and pattern necessary to make a satisfactory reunion of nerve stumps. These lines and pattern indicate the nerve diameter, the general position of the nerve on the device, the distance at which the fixation stitches must be placed from the tip of each stump and the amount of tissue that must be trimmed from the stumps. Thus automatically determined are: the traction on the nerve structures, the compression at the zone of reunion, and the space necessary for expansion in case of post-operative adema. Since the stumps are trimmed after the nerve is fixed on the device, the differences in mechanical and especially elastic properties between the envelopes and the inner structures of the nerve are nullified. Consequently, there is no disruption of the structures and alignment of the nerve, and no interposition of undesired material between the stumps. The surface of the stumps remains absolutely flat after trimming. The space between the point of fixation of the nerve on the device and the tip of the stump allows fine adjustment of the rotational alignment of the stumps. Equipped with a set of connecting devices of the invention for nerves of different diameters, a surgeon is now able to select that connector which provides the proper guide for the particular nerve being rejoined. With the use of such a connector, the surgeon will be able to complete the nerve reunion in the best possible condition. The device can be used alone, or be included in a more complex and sophisticated method of repair.

Although it is anticipated that the present invention will be particularly useful for connecting severed peripheral nerves, it is also contemplated that the invention will be useful for connecting central nerves such as the optic nerve and for rejoining tissues and structures other than nerve tissues and structures. Other uses and applications of the invention will become apparent as the disclosure proceeds.

BEST MODE FOR CARRYING OUT THE INVENTION

Figure 1:
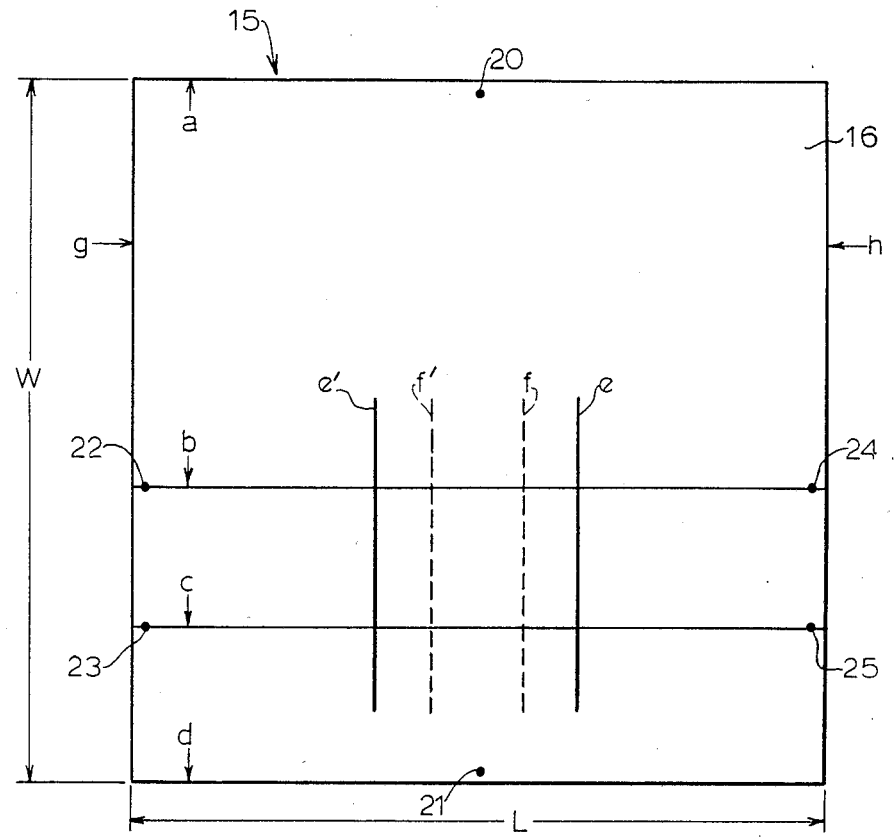
FIG. 1 is a representative illustration of the connector of the present invention.

Making reference to the drawings, the invention connector 15 is made as a 0.1 to 0.4 millimeter thick rectangular plastic sheet 16. Any biocompatible, thin, flexible, non-elastic and non-toxic sheet material could be used. Silastic or polyglycolic acid sheet materials are deemed suitable. Biodegradable materials are considered to be particularly advantageous for the present invention. The guide-measuring lines of the connector 15 may be inscribed on the plastic sheet 16 with a dry point. Alternatively, any biocompatible non-toxic ink, dye or other marking could be used, including inscribing or embossing. The nerve is preferably fixed onto the invention 15 with surgical sutures. Alternatively, the nerve can be fixed onto the connector with a biocompatible glue, mechanical hooks, or other means of fixation suited to the requirements of the invention.

Since one purpose of the connector 15 is to serve as a measuring guide, proper spacing of the guide and measuring lines drawn on the sheet 16 as adapted to each nerve caliber is important. The average diameter of human nerves, as classified according to caliber for purposes of the present invention, is provided, in millimeters, in the following Table 1.

TABLE 1

| Designation | average nerve diameter in mm | fits nerves from mm | to mm | suggested caliber of suture |
|---|---|---|---|---|
| ½ | .70 | .60 | .85 | 11/0 |
| 1 | 1.0 | .85 | 1.2 | 10/0 |
| 1½ | 1.4 | 1.2 | 1.7 | 9/0 |
| 2 | 2.0 | 1.7 | 2.4 | 8/0 |
| 2½ | 2.7 | 2.4 | 3.3 | 8/0 |
| 4 | 3.8 | 3.3 | 4.6 | 7/0 |
| 5 | 5.4 | 4.6 | 6.5 | 6/0 |
| 7 | 7.5 | 6.5 | 9. | 5/0 |
| 10 | 10.5 | 9. | 12.7 | 4/0 |

Connector 15 is constructed in a different size for each of the nine nerve diameter classes specified in Table 1. The precise dimensions can be best understood by making reference to FIG. 1, where lines and edges of the connector 15 are designated with small case letters and suture points with numbers. Distances between the lines and edges are provided as a function of nerve diameter in Table 2 below, so that a set of nine different connecting devices can be constructed from FIG. 1, Table 1, and Table 2. The best mode of carrying out the invention is specified in the left column of Table 2; the range of useful sizes is specified in the right column of Table 2. Length direction is indicated by L and width direction by W.

TABLE 2

| Distances between lines and edges as a function of nerve diameter | Tolerable variations from | to |
| --- | --- | --- |
| gh = 5 | 3.8 | 6.5 |
| ad = 5.25 | 4 | 7 |
| ab = 3 | 2 | 4 |
| bc = 1 | 0.855 | 1.15 |
| cd = 1.25 | 1 | 1.75 |
| ge' = 1.4 | 1 | 2 |
| he = 1.4 | 1 | 2 |
| e'f' = .6 | 0.5 | 0.7 |
| ef = .6 | 0.5 | 0.7 |
| ff' = .5 | 0.4 | 1 |

Thus, for example, a nerve connector 15 constructed for that class of human nerves having an average diameter of 2 mm would be 10 mm long, 10.5 mm wide, have line (c) positioned 2.5 mm above edge (d), have line (e) positioned 2.8 mm from edge (h) and line (e') positioned 2.8 mm from edge (g). There would be a 1.2 mm space between lines (b) and (c). Points 20, 21, 22, 23, 24 and 25 indicate where the stitches are passed through the connector. These points are located 0.125 times the nerve diameter for which the connector 15 has been constructed from the nearest edge of the connector. Thus, in the given example each point would be 0.250 mm from the respective nearest edge. Points 20, 21 are otherwise located midway of the length L and points 22, 24 are located on line B and below the midpoint of width W. In general, the measured length of secured nerve stump prior to trimming would not exceed 4.4 times the nerve diameter and the amount of overlap prior to trimming would be between 0.4 and 1 times the nerve diameter.

The use of the invention connector 15 will be explained with reference to FIGS. 2 through 12. For clarity, lines, points and edges have not been designated with letters and numbers in these figures. FIG. 1 should be referred to whenever a letter or number designation is provided.

Figure 2:
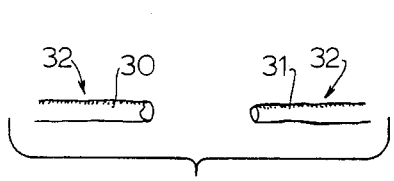
FIG. 2 illustrates the proximal and distal stumps of a transected peripheral nerve.

FIG. 2 illustrates the proximal 30 and distal 31 stumps of a severed peripheral nerve 32. During the surgical preparation of the nerve (and the chemical preparation, if there is one), great care should be taken not to disrupt the mesoneurium binding the nerve elements at the tip of the stumps so as not to modify their relative orientation. The correct rotational positions of the stumps is determined by careful examination of the tips of the stumps. The correct size nerve connector 15 is then chosen by measuring the approximate diameter of the nerve. The size can then be checked by laying the chosen connector 15 under the nerve and making sure that the distance between lines (b) and (c) corresponds approximately to the diameter of the stumps when placed between and parallel to lines (b) and (c). For the purpose of maintaining consistency in the description, it is assumed that the surgeon begins the reunion procedure with the distal stump 31.

Figure 3:
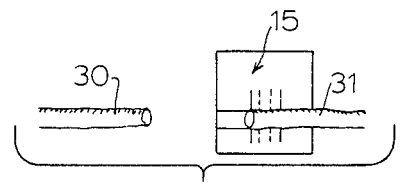
FIG. 3 illustrates the connector aligned beneath the distal stump of a severed nerve.
Figure 4:
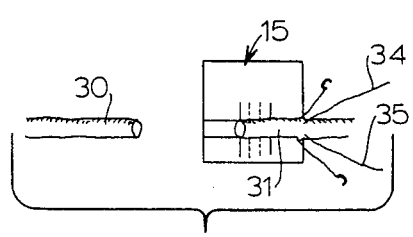
FIG. 4 illustrates the distal stump of a transected nerve being stitched through its epineurial sheath to the invention.
Figure 5:
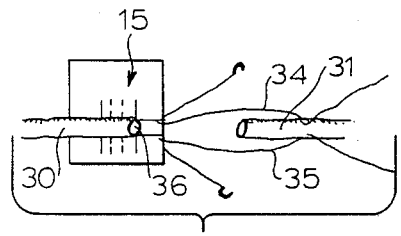
FIG. 5 illustrates the connector sutured to the distal stump of a nerve and pulled up under the proximal stump of the severed nerve.
Figure 6:
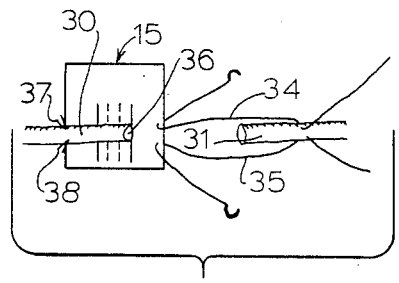
FIG. 6 is similar to FIG. 5, but illustrates the connector stitched to the proximal stump of the severed nerve.
Figure 7:
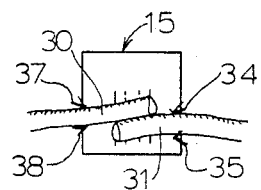
FIG. 7 illustrates the proximal and distal stumps of the transected nerve, as finally fixed to the connector when the stitches are tied, but prior to being trimmed.
Figure 8:
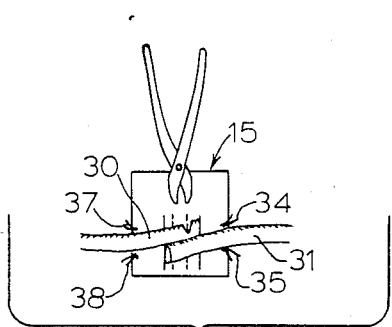
FIG. 8 illustrates the proximal stump of the nerve being trimmed.
Figure 9:
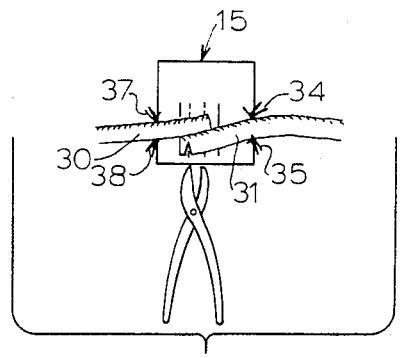
FIG. 9 illustrates the distal stump of the nerve being trimmed.
Figure 10:
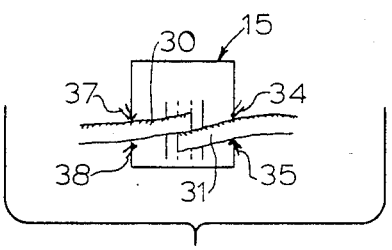
FIG. 10 illustrates the nerve after completion of the trimming steps.
Figure 11:
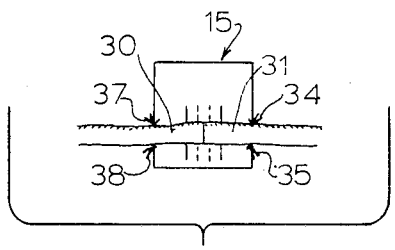
FIG. 11 is similar to FIG. 10, except that the proximal and distal stumps of the severed nerve have been longitudinally aligned and placed in their final tip abutting position.
Figure 12:
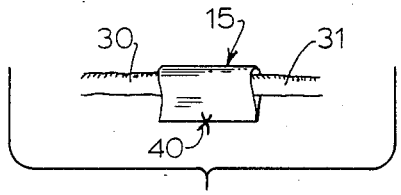
FIG. 12 depicts the two lateral edges of the invention wrapped around the rejoined nerve and stitched together. The extra space around the nerve represents the needed room for expansion in case of post-operative edema.

The connector 15 is correctly positioned below distal stump 31 by placing the distal stump 31 between and generally parallel to lines (b) and (c) in such a way that the tip of this distal stump before trimming comes at line (e') (see FIG. 3). A stitch 34 of appropriate caliber (see Table 1) is then passed through the epineurium on one side and through the connector 15 at point 24. A second stitch 35 is then passed through the epineurium on the other side of the nerve and through the connector at point 25 (see FIG. 4). These stitches are not tied. Rather, the connector 15 is pulled away from distal stump 31 and placed under the proximal stump 30, with the threads 34 and 35 following loosely. The proximal stump 30 is correctly positioned on the connector 15 by aligning proximal stump 30 between and parallel to lines (b) and (c) in such a way that the extremity of the proximal stump 30 before trimming comes on line (e) (see FIG. 5). Two stitches 37 and 38 are passed through the nerve epineurium of the proximal stump 30 and through the connector at points 22 and 23, respectively (see FIG. 6). These stitches are tied. The first two stitches 34 and 35 are then also pulled tight and tied, bringing the stumps to the desired overlap (see FIG. 7). The proximal stump 30 is then trimmed at the level of line (f) (see FIG. 8) and the distal stump 31 is trimmed at the level of line (f') (see FIG. 9). This procedure removes the damaged tips of the nerve stumps and automatically establishes the amount of compression that will exist at the site of reunion (see FIG. 10). The freshly trimmed nerve stumps are then placed end-to-end (see FIG. 11). When the reunion is considered satisfactory, the connector 15 is folded over the nerve and stitched shut with a suture thread going through the connector at points 20 and 21 (see FIG. 12). This procedure inhibits lateral movement of the nerve stumps but permits expansion of the nerve structure in the event of post-operative edema. The wound can then be closed, leaving connector 15 implanted, and usual post-operative procedures followed. Connector 15, if made of the desirable biodegradable material biodegrades in the course of time as the rejoined nerve completes the healing process.

What is claimed is:

1. A method for reconnecting first and second stumps of a transected cable-like structure in the human body, comprising the steps of:
   (a) locating below the first stump of the transected structure to be reconnected a connector formed of flexible, inelastic thin sheet material and having guide-measuring lines inscribed thereon;
   (b) securing a first predetermined guideline measured length of said first stump to said connector at a point removed from the tip of said stump;
   (c) locating the second stump of said structure to be reconnected on said connector and securing a second predetermined guideline measured length of said second stump to said connector at a point removed from the tip of said second stump and spaced some predetermined distance opposite from the point at which said first stump was secured;
   (d) trimming a guideline measured length of tissue from the tip of each said stump to provide some third predetermined length of stump overlapping when the tip ends of said stumps are placed side-by-side, said third predetermined length corresponding to some desired amount of compression in the reconnected structure at the site of reunion of said stumps;

(e) placing said stumps in longitudinal alignment on said connector with the tips thereof in abuttment; and (f) wrapping said connector around said structure to inhibit lateral movement of said stumps while permitting post-operative expansion.

2. The method of claim 1 wherein:
(a) said transected cable-like structure comprises a nerve; and
(b) said stumps comprise transected stumps of said nerve.

3. The method of claim 1 wherein:
(a) said connector is formed of a rectangular sheet of said material having guide points inscribed thereon; and
(b) said first, second and third predetermined lengths are measured by said measuring lines on the surface of said connector on which said stumps are located and said points of securement are determined utilizing guide points on said surface.

4. The method of claim 2 wherein:
(a) said connector is formed of a rectangular sheet of said material; and
(b) said first, second and third predetermined lengths are measured by said measuring lines on the surface of said connector on which said stumps are located and said points of securement are determined utilizing guide points on said surface.

5. The method of claim 2 wherein said nerve stumps are secured by sutures through the perineurium of said nerve.

6. The method of claim 4 wherein the said first and second predetermined lengths of said stumps secured to said connector do not substantially exceed 4.4 times the diameter of said nerve prior to said trimming.

7. The method of claim 4 wherein said third predetermined length of overlapping is substantially within the range of 0.4 to 1 times the diameter of said nerve.

8. A method for reconnecting first and second stumps of a transected nerve, comprising the steps of:
(a) locating proximate the site of reunion a nerve connector formed of flexible, inelastic, thin sheet material having a pair of spaced-apart opposed first and second defined edges and having measuring guidelines and guide points inscribed thereon;
(b) connecting at selected guide points to a first edge of said connector with sutures through the perineurium of said first stump a first predetermined guideline measured length of the first stump extending towards said second edge and with the tip of said first stump being beyond the midpoint between said edges;
(c) locating said connector in said position beneath the said second stump so that said sutures through the perineurium of said first stump loosely connect said first stump to said connector;
(d) connecting at other selected guide points to a second edge of said connector with sutures through the perinerium of the second stump a second predetermined guideline-measured length of the second stump extending towards said first edge and with the tip of said second stump being beyond the midpoint between said edges;
(e) tying said sutures connecting said second stump with said connector;
(f) tightening said sutures securing said first stump to said connector so that said first stump is pulled towards said connector and the tips of said stumps are brought in side-by-side relation;
(g) tying said sutures connecting said first stump with said connector;
(h) trimming tissue from the tips of each of said stumps to establish a precise predetermined guideline-measured length of said stumps;
(i) placing the tips of said stumps into abutment with the axis of said stumps in substantial longitudinal alignment at the site of reunion; and
(j) wrapping said connector around said nerve to inhibit lateral movement of said stumps.

9. A device for reconnecting proximal and distal stumps of a transected nerve, comprising:
(a) a connector formed of a sheet of thin, flexible, inelastic material having opposed first and second edges, said connector providing between said edges a surface suited for receiving and securing said stumps in longitudinal alignment with the tips thereof abutted and being formed for wrapping around said nerve after the reunion of said stumps; and
(b) a nerve connecting guide formed on said connector surface comprising:
(i) a first pair of parallel measuring lines extending between said edges with the space therebetween corresponding to the approximate diameter of a selected size said nerve;
(ii) second stump measuring lines intersecting said first measuring lines and perpendicular thereto and positioned on said surface at locations corresponding to a preferred length of said stumps to be secured to said connector at said edges; and
(iii) third measuring lines located between and parallel to said second measuring lines and positioned for indicating some desired portion of said predetermined length of stumps to be removed prior to effecting said reunion.

10. The device as claimed 9 including guide points located on said first measuring lines proximate said edges indicating preferred points of securing said predetermined lengths of said stumps to said connector surface.

* * * * *

UNITED STATES PATENT OFFICE
CERTIFICATE OF CORRECTION

Patent No. 4,586,504             Dated May 6, 1986

Inventor(s) Luis de Medinaceli

It is certified that error appears in the above-identified patent and that said Letters Patent are hereby corrected as shown below:

Under "OTHER PUBLICATIONS", "Experimental Neurolog" should be --Experimental Neurology-- and "Lus de Medinaceli" should be --Luis de Medinaceli--.

In Column 8, line 52, "The device as claimed 9" should read --The device as claimed in claim 9--. (Applicant's error)

Signed and Sealed this

Twenty-third Day of September 1986

[SEAL]

Attest:

Attesting Officer

DONALD J. QUIGG

Commissioner of Patents and Trademarks